(12) United States Patent
Maniga

(10) Patent No.: US 8,642,097 B1
(45) Date of Patent: Feb. 4, 2014

(54) NATURAL PRODUCT ENERGY DRINK AND METHOD OF USE THEREOF

(71) Applicant: Nyangenya Maniga, Gilbert, AZ (US)

(72) Inventor: Nyangenya Maniga, Gilbert, AZ (US)

( * ) Notice: Subject to any disclaimer, the term of this patent is extended or adjusted under 35 U.S.C. 154(b) by 0 days.

(21) Appl. No.: 13/847,414

(22) Filed: Mar. 19, 2013

(51) Int. Cl.
*A01N 65/00* (2009.01)

(52) U.S. Cl.
USPC ............................................. 424/725

(58) Field of Classification Search
None
See application file for complete search history.

(56) References Cited

U.S. PATENT DOCUMENTS

| | | |
|---|---|---|
| 4,596,812 A | 6/1986 | Chidsey |
| 4,820,512 A | 4/1989 | Grollier |
| 4,828,837 A | 5/1989 | Uster |
| 5,030,442 A | 7/1991 | Uster |
| 5,225,189 A | 7/1993 | Pena |
| 5,620,980 A | 4/1997 | Samour |
| 5,834,014 A | 11/1998 | Weiner |
| 6,465,514 B1 | 10/2002 | Hallam |
| 6,596,266 B2 | 7/2003 | Catalfo |
| 6,946,120 B2 | 9/2005 | Wai-Chiu So et al. |
| 7,442,369 B1 | 10/2008 | Pena |
| 7,749,489 B2 | 7/2010 | Malek |
| 7,803,357 B2 | 9/2010 | Cappello |
| 2005/0079139 A1 | 4/2005 | Jacques |
| 2008/0206156 A1 | 8/2008 | Cronk |

*Primary Examiner* — Michael Meller
(74) *Attorney, Agent, or Firm* — Kevin Hazen

(57) ABSTRACT

A natural product energy drink is provided, which synergistically aids in (1) function of the heart, (2) energy production, such as in muscles, and/or (3) enhances removal of toxic free radicals. For example, the natural product energy drink enhances function of the heart, by the use of $CoQ_{10}$; enables the body to produce more energy through enhanced efficiency of the Krebs cycle, such as by use of L-carnitine; and aids in the removal of waste and/or toxins produced in the body, such as by providing anti-oxidants. Hence, the energy drink synergistically optimizes the heart, muscles, and toxin removal at the same time, which allows the user to prolong duration of exercise, increase intensity of exercise, and recover faster. The natural product, which provides nutrients, is an energy drink that optionally contains no caffeine or sugar while retaining efficacy.

1 Claim, 1 Drawing Sheet

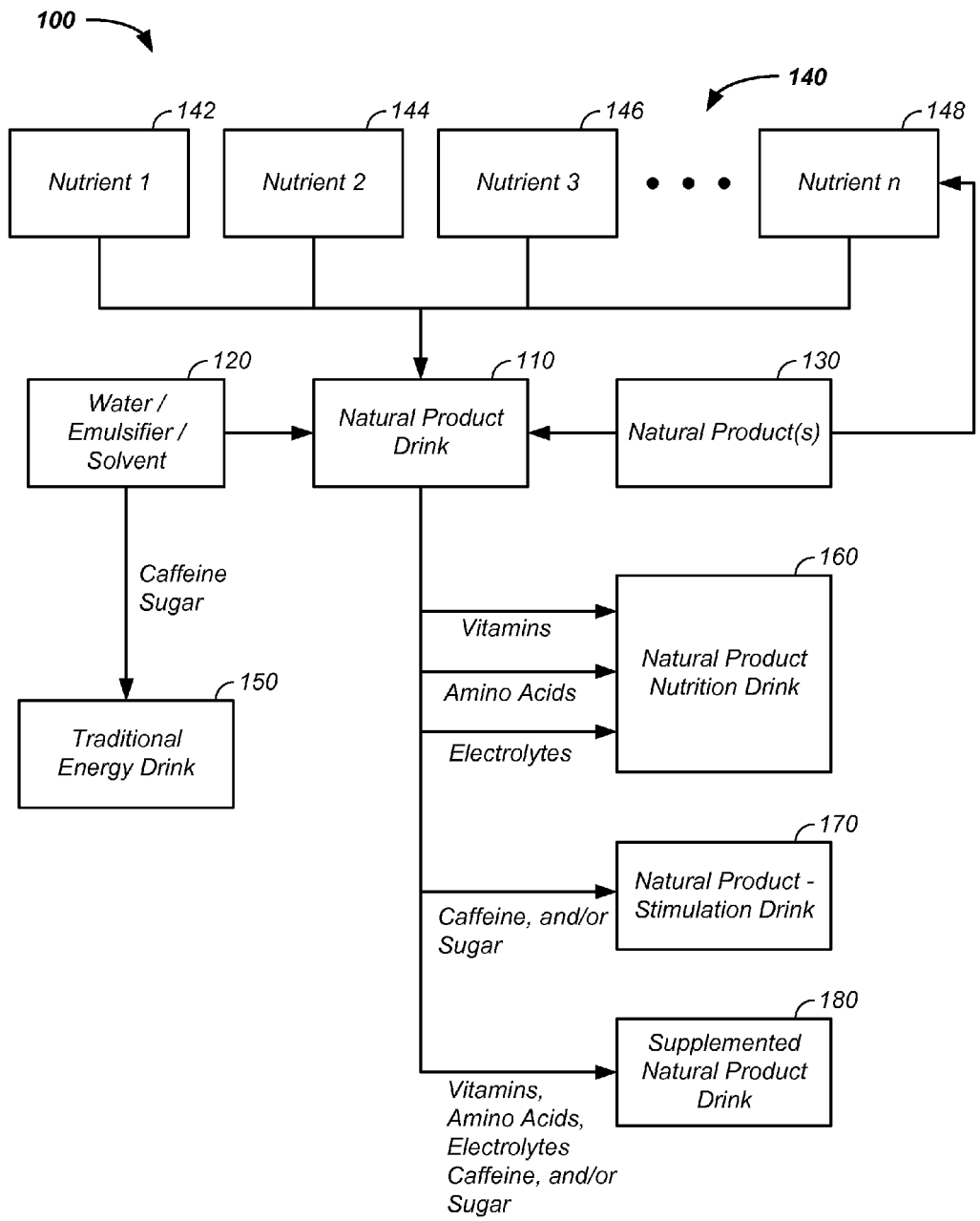

US 8,642,097 B1

NATURAL PRODUCT ENERGY DRINK AND METHOD OF USE THEREOF

CROSS REFERENCES TO RELATED APPLICATIONS

This application claims the benefit of U.S. provisional patent application No. 61/615,271 filed Mar. 24, 2012, all of which is incorporated herein in its entirety by this reference thereto.

TECHNICAL FIELD OF THE INVENTION

The present invention relates to a natural product energy and/or nutrition drink.

DESCRIPTION OF THE RELATED ART

There exist a number of drinks designed to aid human performance. However, the human performance drinks are of three types: (1) those that provide electrolytes; (2) those that provide vitamins; and (3) those that provide energy through use of sugar and caffeine.

Examples of electrolyte providing drinks include drinks providing sodium, potassium, calcium, and magnesium. Brand name examples of electrolyte drinks include: Gatorade and Powerade. In the art, electrolyte providing energy drinks are used to replace electrolytes lost due to sweat.

Examples of vitamin providing drinks include drinks providing vitamin B.

Examples of energy drinks include drinks providing: caffeine and sugar. Brand name examples of energy drinks include: Red Bull® (Red Bull GmbH, Austria), Monster® (Monster Beverage Corporation, Corona, Calif.), Rockstar® (Rockstar Beverage Corporation, Lax Vegas, Nev.), and 5-Hour Energy® (Living Essentials, Wabash, Ind.). In the art, the energy drinks are used to overcome tiredness due to lack of sleep and/or lack of sleep by increasing heart rate and raising sugar levels in the body.

Problem Statement

What is needed is an energy drink that does not overwork the heart or result in a metabolic crash while providing nutrition.

SUMMARY OF THE INVENTION

The invention comprises a natural product energy drink and method of use thereof.

BRIEF DESCRIPTION OF THE DRAWINGS

A more complete understanding of the present invention is derived by referring to the detailed description and claims when considered in connection with the Figures, wherein like reference numbers refer to similar items throughout the Figures.

FIG. 1 illustrates a natural product formulation.

Elements and steps in the figures are illustrated for simplicity and clarity and have not necessarily been rendered according to any particular sequence. For example, steps that are performed concurrently or in different order are illustrated in the figures to help improve understanding of embodiments of the present invention.

DETAILED DESCRIPTION OF THE PREFERRED EMBODIMENTS

The invention comprises a natural product drink.

In one embodiment, one or more natural product constituents are combined with a solvent, such as water to form the natural product drink or natural product energy drink. The natural product energy drink synergistically aids in (1) function of the heart, (2) energy production, such as in muscles, and/or (3) enhances removal of toxic free radicals. For example, the natural product energy drink enhances function of the heart, by the use of $CoQ_{10}$; enables the body to produce more energy through enhanced efficiency of the Krebs cycle, such as by use of L-carnitine; and aids in the removal of waste and/or toxins produced in the body, such as by providing anti-oxidants. Hence, the energy drink synergistically optimizes function of the heart, function of muscle, and toxin removal at the same time, which allows the user to prolong duration of exercise, increase intensity of exercise, and recover faster. The natural product energy drink optionally contains no caffeine or sugar while retaining efficacy.

In another embodiment, the natural product drink is supplemented with one or more vitamins, amino acids, and/or electrolytes, which results in a natural product nutrition drink.

In yet another embodiment, the natural product drink is supplemented with a form of caffeine and/or a form of sugar, which results in a natural product/stimulation energy drink.

In another embodiment, the natural product energy drink is supplemented with (1) one or more vitamins, amino acids, and/or electrolytes and (2) a form of caffeine and/or a form of sugar, which results in a supplemented natural product drink.

Energy Drinks

Referring now to FIG. 1, a flow chart illustrating formation of an energy drink 100 is provided. FIG. 1 contrasts a traditional energy drink 150 from a natural product energy drink 110, each of which are further described infra.

Still referring to FIG. 1, a traditional energy drink 150 is a solution of a solvent 120, such as water, mixed with caffeine and/or sugar.

Still referring to FIG. 1, herein a natural product energy drink 110 is a combination of a solvent 120, a natural product 130, and/or a nutrient 140. The solvent 120 is any liquid, aqueous mix, non-aqueous based solvent, water, an emulsifier, and/or a suspension agent. Herein, a natural product 130 is a chemical, chemical compound, or substance produced by a living organism found in nature. The natural product 130 is produced by a plant or animal. Herein, a nutrient 140 is a product derived from a natural product, is a constituent of a natural product, or is a simulant of a constituent of a natural product. For example, pine bark is a natural product produced by the maritime pine tree (*Pinus pinaster*). An extraction of the natural product 130 of pine bark is pine bark extract, which is a nutrient 140. An example of the extracted constituent is a chemical from the class of extracted naturally occurring chemicals referred to as proanthocyanidins. An artificially produced chemical simulant of a natural product nutrient is a chemical, substance, and/or mixture that retains one or more properties of the nutrient 140, but is man-made. The natural product drink 110 optionally contain 1, 2, 3, ... n nutrients 142, 144, 146, 148, where n is a positive integer. Herein, sugar and caffeine are not in the class of natural products 130.

In stark contrast to a traditional energy drink 150, which contains high concentrations of sugar and/or caffeine, the nutrition energy drink 110 contains no caffeine, no sugar, a low concentration of sugar, a low concentration of caffeine, or a high concentration of sugar with a low concentration of caffeine. Herein, a high concentration of caffeine is the caffeine in a cup of coffee or more and a high concentration of sugar is the concentration of sugar in a traditional non-diet soda. For example, traditional brewed coffee has about 80 to 135 mg of caffeine per serving, which is about 386 to 652 mg of caffeine per liter and traditional coca cola contains 34 mg or caffeine per serving or 96 mg of caffeine per liter. Traditional energy drinks 150 contain higher amounts of caffeine per serving and higher concentrations of caffeine. For example, Red Bull contains 80 mg or caffeine per serving and 320 mg of caffeine per liter. In stark contrast, the nutrition energy drink preferably contains no caffeine per serving and optionally contains less than 1, 2, 4, 8, 10, 15, 20, or 25 mg of caffeine per serving or less than 5, 10, 20, 40, 60, or 80 mg of caffeine per liter.

Still referring to FIG. 1, a natural product energy drink 110 is optionally combined with: (1) vitamins to form a vitamin enhanced natural product drink, (2) amino acids to form an amino acid enhanced natural product drink or protein enhanced natural product drink, or (3) electrolytes to form an electrolyte enhanced natural product drink. Generally, the natural product drink 110 is optionally supplemented with vitamins, amino acids (such as L-leucine), electrolytes, and/or an additive to form a natural product nutrition drink 160.

Still referring to FIG. 1, a natural product energy drink 110 is optionally combined with: caffeine and/or sugar to form a natural product—stimulation drink 170.

Still referring to FIG. 1, a natural product energy drink 110 is optionally combined with both (1) any of: vitamins, amino acids electrolytes and (2) any of caffeine and/or sugar to form a supplemented natural product drink 180.

In still yet another embodiment, the supplemented natural product drink includes one of more of a form of: a methylxanthine, caffeine, a B vitamin, an herb, carbonated water, guarana, *yerba mate, açaí*, taurine, ginseng, maltodextrin, inositol, carnitine, creatine, glucuronolactone, *ginkgo biloba*, sugar, and artificial sugar.

Natural Products

Generally, a natural product is chemical compound or substance produced by a living organism. A natural product can be considered as such even if it can be prepared by total synthesis. Herein, natural products used in the natural product drink 110 include energy ingredients and/or anti-oxidant ingredients.

Examples of energy inducing natural products used in the natural product drink 110 include, but are not limited to, a form of: ginseng, French pine bark, grape seed, pine bark, and a *Stevia* herb or shrub. Examples of a nutrient 140 is an extract, laboratory produced product, or simulant of a constituent or extract of any natural product. Examples of a nutrient include, but are not limited to: a betaine, a carnitine, a choline, a form of coenzyme $Q_{10}$, an inositol, L-carnitine, a pyruvate, a taurine, and/or an extract, such as a ginseng extract, a grape seed extract, a pine bark extract, and/or a *Stevia* extract. Herein, amino acids, caffeine, sugar, and vitamins are preferably not included in the basic natural product drink 110; however, they are optionally included in a supplemented form of the natural product energy drink, as described supra.

Examples of an anti-oxidant used in the natural product drink include, but are not limited to: a super anti-oxidant, a form of alpha lipoic acid, an extract of Noni, pomegranate, a resveratorol, a resveratrol, and/or tea, such as a green tea, or an extract of Noni, pomegranate, and/or tea.

The concentration of any of the natural product 130, nutrients 140, or additives in the natural product drink 110 or a derivative thereof is in the range of zero to ten percent and more preferably in the range of 0.001 to 10 percent, and still more preferably some of the constituents are in the range of 2 to 5 percent. Similarly, the concentration of any of the natural product 130, nutrients 140, or additives in the natural product drink 110 or a derivative thereof is in the range of zero to ten mg/dose and more preferably in the range of 0.001 to 10 mg/dose, and still more preferably in the range of 0.01 to 7 mg/dose, and yet still more preferably in the range of 0.1 to 6 mg/dose, and still yet more preferably where some of the constituents are in the range of 2 to 5 mg/dose.

Function

A traditional energy drink 150 uses caffeine, which is a stimulant, and/or sugar. The effect of the traditional energy drink 150 is merely to pump more blood, which supplies more oxygen. However, if the body is depleted of nutrition, the traditional energy drink 150 has no effect. In stark contrast, the natural product energy drink 110 provides nutrients to the blood. For example, the natural product energy drink 110 enhances function of the heart, by the use of $CoQ_{10}$. Further, the natural product energy drink 110 enables the body to produce energy through enhanced efficiency of the Krebs cycle, through enhanced production of energy in muscles, and through the increased use of fat as a fuel, such as by use of L-carnitine. Hence, the energy drink synergistically optimizes the heart and muscles at the same time. Still further, the natural product energy drink 110 aids in the removal of waste and/or toxins produced in the body, such as by providing anti-oxidants. As a result, in one example the natural product energy drink 110 aids in function of the heart and muscles at the same time, which enhances the ability to exercise, while simultaneously aiding in the removal of toxic free radicals, such as those produced in exercise, from the body. For example, the body makes its energy at the cellular level (mitochondria) through the Krebs cycle. The ingredients in the natural product energy drink are those that the body uses in its metabolism of energy derived from the Krebs cycle. They work to synergistically balance use of B vitamins and super-antioxidants, such as coenzyme $Q_{10}$ and L-carnitine. At the same time, the natural product energy drink increases the release of energy from food efficiently, such as by enabling the body to convert fats and carbohydrates into energy. Ultimately the result is abundant energy and less fatigue and more muscle with less fat.

In various forms, the natural product energy drink 110 aids in metabolism, fat burning, and/or in providing cellular energy.

Metabolism

In another example, the natural product energy drink 110 is composed of at least three important nutrient groups for a healthy metabolism, liver, and heart. These ingredient groups are:

lipotropic ingredients for the efficient transfer of fats and toxins from the liver;

vitamin B complex and/or amino acids necessary for efficient metabolism of fats and carbohydrates into energy; and super anti-oxidants, which protect the liver and body tissues from damage from free radicals, which ensures healthy liver, blood vessels and heart, and which contributes to low levels of LDL cholesterol, homocysteine, and triglycerides all of which contribute to heart disease.

The combination of these ingredients helps to increase fat burning into energy leading to a lean body, healthy blood vessels, and a healthy heart.

Fat Removal and Burning

In another example, the natural product energy drink 110 contains lipotropic ingredients, which aid the liver by dissolving, removing, and/or burning off fats for energy. The lipotropic ingredients also prevent fat deposition onto the liver. These events lead to low levels of fat deposition in the body and hence loss of weight. Optional lipotropic ingredients in the natural product energy drink 110 include, but are not limited to, one or more of:

betaine, also called trimethyl glycine (TMG), which is a methyl donor for tissue repair and which reduces homocysteine levels;

inositol, which reduces fat infiltration of the liver by the dissolution, transfer, and metabolism of liver fat;

L-methionine, which detoxifies and helps to regenerate live cells, repairs and reverses damaged liver cells, helps to lower cholesterol, and protects against a fatty liver; and choline, which helps transport fat from the liver, is a methyl donor and precursor to acetylcholine, and is necessary for liver regeneration and overall health.

Cellular Energy

In yet another example, the natural product energy drink 110 aids in production of energy at the cellular level through the Krebs cycle. For instance, the natural product energy drink 110 ingredients include a B12 lipotropic complex that the body uses in its metabolism of energy derived from the Krebs cycle, which increases the release of energy from food efficiently, enables the body to convert fats and carbohydrates into energy, and ultimately results in abundant energy, less fatigue, more muscle, and less fat.

Benefits

Observed benefits of the natural product energy drink 110 include: ability to exercise for longer duration, ability to exercise with increased intensity, reduced recovery time, decrease in cholesterol, a decrease in blood pressure, an enhanced ability to sleep, an increased mental alertness, and/or an increased sexual drive. Simply, it improves the overall health of the body. Taken early in the morning, during the day, and/or before exercise, the body's endurance and resistance to fatigue is increased.

Form

The natural product energy drink 110 is optionally used in a number of forms. For clarity, the description herein is provide for the natural product energy drink 110 in a solution that is ready to drink, from a small container, in a dilute form from a larger container, or as a teaspoon dose. However, the natural product energy drink 110 is optionally provided in alternative forms. First, the natural product energy drink 110 is optionally provided as a concentrate, allowing the user to mix with water or into a food or beverage. The concentrate is at least 2, 3, 4, 5, 10, 15, or 20 times the concentration of the above described ready to drink formulation. Second, the natural product energy drink 110 is optionally provided in the form of a sublingual spray. Third, the natural product energy drink 110 is optionally provided in powder form, which is mixed by the user as needed into a solution, is added directly to a food substrate, or is directly ingested. Optionally, the formulation is contained in a gauze bag, suitable for brewing like that of a tea bag and/or coffee pod. Optionally, the formulation is contained as a dry powder in a pouch, such as an easy tear open flexible mini-pouch containing one or more servings.

Packaging for the formulation includes any package or container for holding a solid, liquid, emulsion, suspension, or the like, such as a can, a bottle, a pouch, gauze bag, or a packet. The packaging is optionally for bulk product, multiple servings, or single dose.

Spray Bottle

Optionally, the formulation is maintained in a liquid form deliverable via a spray bottle, such as a sublingual spray delivery bottle. In one example, the spray bottle contains a manual pump, a pressurized pump, and/or an air pressurized fluid delivery system. For clarity of presentation, a manual pump spray bottle is further described herein without loss of generality. The pump is attached to a tube, such as a plastic tube, that draws a liquid form of the formulation from a bottom of a reservoir in the spray bottle container. The pump forces the liquid formulation down a narrow barrel and out a small hole at a muzzle of the spray bottle. The hole, nozzle, and/or aperture serves to focus the flowing liquid into an accelerated stream suitable for sublingual spray delivery. The pump optionally includes a piston housed inside a cylinder, typically with a small spring. To operate the pump, the pump is depressed pushing the piston into the cylinder. The moving piston compresses the spring, so when you release the trigger, the piston is pushed back out of the cylinder. These two strokes of the piston, into the cylinder and out again, constitute the entire pump cycle. For example, in the downstroke, the piston pushes in, shrinks the area of the cylinder, and forces fluid out of the pump and in the upstroke the spring pushes the piston back out, expands the cylinder area, and sucks fluid into the pump. In the sublingual spray bottle, the pump only forces the fluid up in one direction and not back into the reservoir using a one-way valve. Optionally, the spray bottle has two one-way valves in the pumping system: one between the pump and the reservoir and one between the pump and the nozzle. Typically, the valve between the pump and the reservoir includes a tiny rubber ball that rests neatly inside a small seal. The sides of the seal are angled so that the ball won't fall through. Depending on the design, either gravity or a small spring holds this ball against the seal so that the water passageway is blocked off when the operator is not pumping. When the piston moves out, such as when an operator releases the trigger or pump, the expanding area of the cylinder sucks on the fluid below, pulling the ball up out of the seal. Since the ball is lifted up, fluid is free to flow from the reservoir. However, when the operator squeezes the pump, the outward force of the moving fluid pushes the ball into the seal, blocking off the passageway to the reservoir. Consequently, the pressurized fluid is pushed only into the barrel and subsequently out of the spray nozzle.

Liquid Dropper Bottle

In yet another embodiment, the formulation is contained in a bottle as a fluid, where the bottle contains a liquid dropper tube, such as a sublingual liquid dropper delivery tube tapered at one end with a bulb for forcing air/fluid movement relative to the tube on the opposite end, which is a liquid dropper suitable for delivery of the liquid formulation under the tongue of an individual.

Still yet another embodiment includes any combination and/or permutation of any of the energy drink and/or nutrition drink constituents described herein.

The particular implementations shown and described are illustrative of the invention and its best mode and are not intended to otherwise limit the scope of the present invention in any way. Indeed, for the sake of brevity, conventional manufacturing, connection, preparation, and other functional aspects of the system may not be described in detail. Furthermore, the connecting lines shown in the various figures are intended to represent exemplary functional relationships and/or physical couplings between the various elements. Many alternative or additional functional relationships or physical connections may be present in a practical system.

In the foregoing description, the invention has been described with reference to specific exemplary embodiments; however, it will be appreciated that various modifications and changes may be made without departing from the scope of the present invention as set forth herein. The description and figures are to be regarded in an illustrative manner, rather than a restrictive one and all such modifications are intended to be included within the scope of the present invention. Accordingly, the scope of the invention should be determined by the generic embodiments described herein and their legal equivalents rather than by merely the specific examples described above. For example, the steps recited in any method or process embodiment may be executed in any order and are not limited to the explicit order presented in the specific examples. Additionally, the components and/or elements recited in any apparatus embodiment may be assembled or otherwise operationally configured in a variety of permutations to produce substantially the same result as the present invention and are accordingly not limited to the specific configuration recited in the specific examples.

Benefits, other advantages and solutions to problems have been described above with regard to particular embodiments; however, any benefit, advantage, solution to problems or any element that may cause any particular benefit, advantage or solution to occur or to become more pronounced are not to be construed as critical, required or essential features or components.

As used herein, the terms "comprises", "comprising", or any variation thereof, are intended to reference a non-exclusive inclusion, such that a process, method, article, composition or apparatus that comprises a list of elements does not include only those elements recited, but may also include other elements not expressly listed or inherent to such process, method, article, composition or apparatus. Other combinations and/or modifications of the above-described structures, arrangements, applications, proportions, elements, materials or components used in the practice of the present invention, in addition to those not specifically recited, may be varied or otherwise particularly adapted to specific environments, manufacturing specifications, design parameters or other operating requirements without departing from the general principles of the same.

Although the invention has been described herein with reference to certain preferred embodiments, one skilled in the art will readily appreciate that other applications may be substituted for those set forth herein without departing from the spirit and scope of the present invention. Accordingly, the invention should only be limited by the Claims included below.

The invention claimed is:

1. A composition for enhancing function of the heart in a human consisting essentially of therapeutically effective amounts of pine bark extract, grape seed extract, *stevia* extract, coenzyme Q10, *noni* extract, resveratrol, *acai* extract, *yerba mate'* extract and *ginkgo biloba* extract.

* * * * *